United States Patent [19]

Fujii et al.

[11] Patent Number: 4,539,403
[45] Date of Patent: Sep. 3, 1985

[54] PROCESS FOR THE PREPARATION OF A 2-ALKYL-4-AMINO-5-AMINOMETHYL-PYRIMIDINE

[75] Inventors: Kozo Fujii; Keigo Nishihira; Hiroyuki Sawada; Shuji Tanaka; Mamoru Nakai; Hiroshi Yoshida; Teruhiko Inoue; Kiyosi Oomori, all of Ube, Japan

[73] Assignee: UBE Industries, Ltd., Tokyo, Japan

[21] Appl. No.: 461,163

[22] Filed: Jan. 26, 1983

[30] Foreign Application Priority Data

Feb. 16, 1982 [JP] Japan ................... 57-22122
Sep. 7, 1982 [JP] Japan ................... 57-154661
Sep. 14, 1982 [JP] Japan ................... 57-158916

[51] Int. Cl.³ .......................................... C07D 239/02
[52] U.S. Cl. .................................. 544/326; 564/397; 564/398; 564/472; 564/473
[58] Field of Search ............... 544/326; 564/472, 473, 564/397, 398

[56] References Cited

U.S. PATENT DOCUMENTS 3,223,734  12/1965  Fallstad ................... 564/480
4,210,605  7/1980   Hoshino ................... 564/473

OTHER PUBLICATIONS

Groggins, Unit Process in Organic Synthesis, 5th Edition, pp. 408–409, 1958.
Morrison, Organic Chemistry, p. 733.
Huber, J.A.C.S. 66,876, 1944.

*Primary Examiner*—Donald G. Daus
*Assistant Examiner*—Cecilia Shen
*Attorney, Agent, or Firm*—Frishauf, Holtz, Goodman & Woodward

[57] ABSTRACT

There is disclosed a process for the preparation of a 2-alkyl-4-amino-5-aminomethylpyrimidine, which comprises subjecting a 2-alkyl-4-amino-5-formylpyrimidine to catalytic reaction with hydrogen and ammonia in the presence of a reduction catalyst.

According to the process of this invention, the desired product can be obtained in much higher yield as compared with the processes known to the art.

26 Claims, No Drawings

PROCESS FOR THE PREPARATION OF A 2-ALKYL-4-AMINO-5-AMINOMETHYLPYRIMIDINE

This invention relates to a novel process for the preparation of a 2-alkyl-4-amino-5-aminomethylpyrimidine. It has been known that a 2-alkyl-4-amino-5-aminomethylpyrimidine is an important intermediate for the syntheses of Vitamin $B_1$ and its analogues (Encyclopedia of Chemical Technology, Second Edition, vol 20, 173 (1969), John Wiley & Sons, Inc.).

As methods for preparing a 2-alkyl-4-amino-5-aminomethylpyrimidine, there have hitherto been known, for instance, a process in which a 2-alkyl-4-amino-5-cyanopyrimidine is reduced (Yakugaku Zasshi (Journal of Pharmaceutics), Japan, 73, 977 (1953), J.A.C.S. 66 876 (1944)); a process in which a 2-alkyl-4-amino-5-acetamidomethylpyrimidine is hydrolyzed (Chem. Ber. 106 893 (1973)); and so on.

The present inventors have made earnest studies for the purpose of developing a novel process for the preparation of a 2-alkyl-4-amino-5-aminomethylpyrimidine.

As the result, they have found that a 2-alkyl-4-amino 5-aminomethylpyrimidine may be prepared in much higher yield as compared with the processes known to the art, by subjecting a 2-alkyl-4-amino-5-formylpyrimidine to reductive amination by catalytic reaction with hydrogen and ammonia in the presence of a reduction catalyst, and accomplished the present invention.

The starting material, i.e., the 2-alkyl-4-amino-5-formylpyrimidine used in the present invention, has the following structural formula:

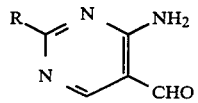

wherein R includes a lower-alkyl group such as methyl, ethyl, propyl and butyl.

The starting material may easily be synthesized, for example, by hydrolyzing a 2-alkyl-4-amino-5-dialkoxymethylpyridine in the presence of an acid. The starting 2-alkyl-4-amino-5-formylpyrimidine may also be employed in the form of a salt with a mineral acid such as sulfuric acid, nitric acid, hydrochloric acid, phosphoric acid and the like.

As the reduction catalyst used in the present process, there may be used a VIII group metal such as palladium, platinum, rhodium, ruthenium, nickel, cobalt and iron; and a metal such as copper and chromium. These metals are usually employed in the form of a metal per se. However, they may also be used in the form of a salt, an oxide or an alloy. Further, nickel may be in the form of a Raney-Nickel which has been developed according to an ordinary method known to the art. These catalysts may be employed alone or in admixture of two or more kinds thereof. Further, the catalyst may also be activated by, for example, hydrogen prior to the use thereof. Furthermore, these catalysts may also be employed after supported on a carrier such as an activated carbon, alumina, silica, silicon carbide, diatomaceous earth, pumice stone, zeolite, molecular sieves and the like.

The catalyst may typically be used in an amount of 0.001 to 3 gram atoms, preferably of 0.002 to 2 gram atoms in terms of the metal, per one mole of the starting 2-alkyl-4-amino-5-formylpyrimidine.

The hydrogen may typically be used in an amount of not less than one mole, preferably of 5 to 400 moles per one mole of the starting 2-alkyl-4-amino-5-formylpyrimidine. The ammonia may be used in the form of a liquid ammonia, an ammonia gas or an aqueous ammonia, in an amount of not less than one mole, preferably of 4 to 500 moles per one mole of the starting 2-alkyl-4-amino-5-formylpyrimidine.

The reaction may be carried out in a solvent inert to the reaction. The solvents includes a lower aliphatic alcohol such as methanol, ethanol, propanol and butanol; an ether such as dioxane, tetrahydrofuran and diethyl ether; a hydrocarbon such as benzene, toluene, xylene, hexane and cyclohexane; and water.

The reaction is carried out at a temperature of 0 to 200° C., preferably room temperature to 120° C. While the reaction proceeds even under ambient pressure, it usually is carried out under a partial pressure of hydrogen of 1 to 100 $Kg/cm^2G$ since the reaction can proceed more speedily under positive pressure. For the reaction, a period of around 0.5 to 10 hours is sufficient.

According to a preferred embodiment of the present invention, the reduction reaction of the 2-alkyl-4-amino-5-formylpyrimidine is carried out in the presence of a salt of divalent nickel ($Ni^{++}$) in addition to the reduction catalyst mentioned above.

As the salt of divalent nickel to be used in the present invention, there may be mentioned nickel chloride, nickel bromide, nickel sulfate, nickel nitrate, nickel phosphate, nickel carbonate, nickel hydroxide, nickel acetate, nickel oxalate, nickel benzoate, nickel ammonium chloride, nickel ammonium sulfate, nickel potassium sulfate and so on. These salts of divalent nickel may be employed alone or in combination of two or more kinds thereof. These divalent nickel salts may be used in the form of a hydrate (one which has a crystalline water). The amount of the salt to be used is in the range of 0.1 to 5 moles, preferably 0.4 to 1.0 mole per one mole of the starting 2-alkyl-4-amino-5-formylpyrimidine. If the amount is smaller than the lower limit of the above-mentioned range, it is not so expected that the suppression of the formation of such by-products as 2-alkyl-4-amino-5-hydroxymethylpyrimidine, di-(2-alkyl-4-amino-5-pyrimidylmethyl)amine and the like will be effected. On the other hand, if the amount is larger than the upper limit of the abovementioned range, the yield of the desired product is liable to be decreased.

As the reaction procedure, there may be carried out, for example, a process in which a 2-alkyl-4-amino-5-formylpyrimidine is reacted with ammonia and hydrogen at the same time or a process in which a 2-alkyl-4-amino-5-formylpyrimidine is reacted first with ammonia followed by the reaction with hydrogen by introducing the same into the system, both in the presence of a salt of divalent nickel and a reduction catalyst. Further, the reaction may also be carried out by subjecting first a 2-alkyl-4-amino-5-formylpyrimidine to reaction with ammonia in the presence of a salt of divalent nickel followed by the reaction with hydrogen while introducing the same into the system after addition of a reduction catalyst thereto.

According to another preferred embodiment of the present invention, the preparation of the 2-alkyl-4-amino-5-aminomethylpyrimidine is carried out by subjecting the 2-alkyl-4-amino-5-formylpyrimidine to reaction with ammonia in an inert solvent, adding the thus obtained reaction product, without isolating the same from the reaction mixture, to an inert solvent containing ammonia, hydrogen and the reduction catalyst mentioned above to reduce the reaction product mentioned above.

In the process according to the preferred embodiment, the 2-alkyl-4-amino-5-formylpyrimidine is reacted first with ammonia in an inert solvent.

The ammonia may be used in the form of a liquid ammonia, an ammonia gas or an aqueous ammonia, in an amount of not less than one mole preferably of 4 to 500 moles per one mole of the starting 2-alkyl-4-amino-5-formylpyrimidine.

The inert solvent may include the same as mentioned previously.

The amount of the solvent to be used may preferably be in the range of 3 to 30 parts by weight per one part by weight of the starting 2-alkyl-4-amino-5-formylpyrimidine.

The first reaction with ammonia is carried out at a temperature of 0° to 130° C., preferably room temperature to 110° C. While the reaction proceeds under ambient pressure, it usually is carried out under a partial pressure of ammonia of 1 to 100 Kg/cm$^2$G since the reaction can proceed more speedily under positive pressure. For the reaction, a period of around 0.5 to 10 hours is sufficient.

It may be supposed that the 2-alkyl-4-amino-5-formylpyrimidine has been converted, by the reaction, into an aldimine represented by the following general formula:

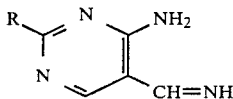

wherein R has the same meaning as defined above.

Next, the reaction mixture containing a reaction product which is supposed to be represented by the above general formula is added, optionally after removing the ammonia insoluble in the inert solvent, to an inert solvent containing ammonia, hydrogen and a reduction catalyst to reduce the reaction product mentioned above. The addition may be carried out by adding the reaction mixture containing the above-mentioned reaction product at one time. However, it usually is preferred to introduce it gradually and continuously over around 0.5 to 8 hours.

The catalyst may typically be used in the same amount as mentioned previously.

As the ammonia, a liquid ammonia, an ammonia gas and an aqueous ammonia may be used like they are used in the step of the reaction between the above-mentioned 2-alkyl-4-amino-5-formylpyrimidine and ammonia. The amount thereof to be used is not less than one mole, preferably 4 to 300 moles per one mole of the starting 2-alkyl-4-amino-5-formylpyrimidine.

The hydrogen may typically be used in the same amount as mentioned previously.

The inert solvent used in this step of procedure may preferably be the same as used in the step of the reaction between the above-mentioned 2-alkyl-4-amino-5-formylpyrimidine and ammonia. The amount thereof to be used may preferably be in the range of 2 to 20 parts by weight per one part by weight of the starting 2-alkyl-4-amino-5-formylpyrimidine.

The reaction in this second step is carried out at a temperature of 0° to 200° C., preferably room temperature to 120° C. While the reaction may proceed under ambient pressure, it usually is carried out under a partial pressure of hydrogen of 1 to 100 Kg/cm$^2$G. It may be sufficient to carry out the reaction for around 0.5 to 2 hours after addition of the reaction mixture containing the reaction product obtained from a 2-alkyl-4-amino-5-formylpyrimidine and ammonia.

The salt of divalent nickel mentioned above may optionally be added to the reaction system of the above-mentioned first and/or second steps of the reaction, in order to enhance the yield of the desired product.

After completion of the reaction, the 2-alkyl-4-amino-5-aminomethylpyrimidine represented by the following general formula may be obtained in a free form or in the form of a salt with a mineral acid, for instance, by isolating it according to an ordinary method after cooling the reaction mixture and then removing the insolubles such as the catalyst by filtration.

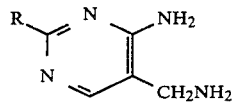

wherein R has the same meaning as defined above.

Next, the Examples of the present invention will be described below. In each Example, the yield of the product is based on the 2-alkyl-4-amino-5-formylpyrimidine used as the starting material.

EXAMPLE 1

In a 100 ml of an autoclave made of stainless steel were introduced 1.37 g (10 mmoles) of 2-methyl-4-amino-5-formylpyrimidine, 15 ml of methanol (solvent) and 0.5 g of a catalyst in which 5 wt % of palladium had been supported on an activated carbon, and the atmosphere within the system was replaced by nitrogen gas followed by addition thereto of 13.4 g of a liquid ammonia.

While stirring the contents, the temperature was raised and maintained at around 60° C. for 1 hour. Thereafter, hydrogen gas was pressured thereinto at the same temperature so that the pressure might be around 40 Kg/cm$^2$G, and the reaction was carried out at the same temperature for 3 hours.

After completion of the reaction, the reaction mixture was cooled and the unreacted ammonia gas and hydrogen gas are purged and released. Then the autoclave was opened and the catalyst was filtered off. Subsequently, a 1N-HCl was added to the filtrate, and the mixture was adjusted to pH at around 3.

Then, the yields of the desired product, 2-methyl-4-amino-5-aminomethylpyrimidine and the by-product, 2-methyl-4-amino-5-hydroxymethylpyrimidine were determined quantitatively as a dihydrochloride and a monohydrochloride, respectively, according to an internal standard method by way of liquid chromatography.

As the result, it was confirmed that the 2-methyl-4-amino-5-aminomethylpyrimidine and the 2-methyl-4-amino5-hydroxymethylpyrimidine had been produced in yields of 90% and 5%, respectively.

EXAMPLE 2

An experiment was run in the same manner as in Example 1 except that 1.51 g (10 mmoles) of 2-ethyl-4-amino-5-formylpyrimidine was used as the starting material in place of the 2-methyl-4-amino-5-formylpyrimidine and that 15 ml of ethanol was used as the solvent in place of the methanol.

As the result, it was found that 2-ethyl-4-amino-5-aminomethylpyrimidine had been produced in a yield of 91% and that 2-ethyl-4-amino-5-hydroxymethylpyrimidine had been by-produced in a yield of 4.5%.

EXAMPLE 3

In a 100 ml of an autoclave made of stainless steel were introduced 1.37 g (10 mmoles) of 2-methyl-4-amino-5-formylpyrimidine, 15 ml of ethanol (solvent) and 1.0 g of Stabilized Nickel (trade name, N103; manufactured by Nikki Kagaku Co., Ltd.; nickel: around 50 wt % and diatomaceous earth: around 50 wt %). After the atmosphere within the system was replace by nitrogen gas, 9.0 g of a liquid ammonia was added thereto. While stirring the contents, the temperature was raised and then maintained at around 90° C. for 30 minutes. Then, a hydrogen gas was pressured thereinto at the same temperature so that the pressure might be around 50 $Kg/cm^2G$, and the reaction was carried out at the same temperature for 2 hours.

Treatment after completion of the reaction was carried out in the same manner as in Example 1.

As the result, it was confirmed that 2-methyl-4-amino-5-aminomethylpyrimidine and 2-methyl-4-amino-5-hydroxymethylpyrimidine had been produced in yields of 89% and 5%, respectively.

EXAMPLE 4

An experiment was run in the same manner as in Example 1 except that 1.0 g of a catalyst in which 5 wt % of platinum had been supported on alumina was used as the catalyst in place of the Stabilized Nickel.

As the result, it was found that 2-methyl-4-amino-5-aminomethylpyrimidine and 2-methyl-4-amino-5-hydroxymethylpyrimidine had been produced in yields of 87% and 6%, respectively.

EXAMPLE 5

An experiment was run in the same manner as in Example 3, except that 1.0 g of a copper-chromium powder was used as the catalyst in place of the Stabilized Nickel and that the pressure of the charged hydrogen gas was changed to be around 80 $Kg/cm^2G$.

As the result, it was found that 2-methyl-4-amino-5-aminomethylpyrimidine had been produced in a yield of 77% and that 2-methyl-4-amino-5-hydroxymethylpyrimidine was by-produced in a yield of 20%.

EXAMPLE 6

In a 100 ml of an autoclave made of stainless steel were introduced 1.74 g(10 mmoles) of 2-methyl-4-amino-5formylpyrimidine hydrochloride, 25 g of a 28 wt % aqueous ammonia and 1.0 g of a Raney-Nickel (nickel content: around 40 wt %) which had been developed and washed with water (water: around 5 ml). After the atmosphere within the system was replaced by nitrogen gas, hydrogen gas was pressured thereinto so that the pressure might be around 40 $Kg/cm^2G$. Subsequently, the temperature of the contents was raised with stirring, and the reaction was carried out at around 90° C. for 3 hours. After-treatment was conducted in the same manner as in Example 1.

As the result, it was found that 2-methyl-4-amino-5-aminomethylpyrimidine had been produced in a yield of 74% and that 2-methyl-4-amino-5-hydroxymethylpyrimidine was by-produced in a yield of 14%.

EXAMPLE 7

In a 100 ml autoclave made of stainless steel, there were introduced 1.37 g (10 mmoles) of 2-methyl-4-amino-formylpyrimidine, 30 ml of a 17 wt % methanolic solution of ammonia and a catalyst which had been prepared by developing 2.0 g of a Raney-Nickel (nickel content: around 40 wt %) followed by water-washing and replacement of the water with methanol (methanol: around 8 ml). Then, the temperature of the contents was raised with stirring, and the temperature was maintained at around 90° C. for 30 minutes. Thereafter, a hydrogen gas was pressured thereinto at the same temperature so that the pressure might be around 40 $Kg/cm^2G$, and the reaction was carried out at the same temperature for 2 hours. Treatment after completion of the reaction was conducted in the same manner as in Example 1.

As the result, it was found that 2-methyl-4-amino-5-aminomethylpyrimidine and 2-methyl-4-amino-5-hydroxymethylpyrimidine had been produced in yields of 85% and 4%, respectively.

EXAMPLE 8

In a 100 ml autoclave made of stainless steel were introduced 1.37 g (10 mmoles) of 2-methyl-4-amino-5-formylpyrimidine, 24 g of a 20 wt % solution of ammonia in methanol and 0.74 g (5.7 mmoles) of anhydrous nickel chloride. After the atmosphere within the system was replaced by nitrogen gas, the temperature of the contents was raised with stirring and maintained at around 90° C. for one hour. After cooling, the autoclave was opened and 0.46 g of Stabilized Nickel (trade name, N103B; manufactured by Nikki Kagaku Co., Ltd.; nickel: around 50 wt %, diatomaceous earth: around 50 wt %). After the atmosphere within the system was replaced by nitrogen gas, hydrogen gas was pressured thereinto so that the pressure might be around 30 $Kg/cm^2G$. Then, the temperature of the content was raised with stirring and the reaction was carried out at around 90° C. for 2 hours.

After completion of the reaction, the reaction mixture was cooled and then unreacted gases etc. were purged and released from the autoclave. Thereafter, the autoclave was opened and the catalyst was filtered off. After the washing obtained when the catalyst was washed with methanol was combined with the filtrate, the so combined liquid was concentrated under reduced pressure to remove major part of the ammonia. Then, a 1N-HCl was added thereto to adjust the pH at around 3, and the mixture was subjected to liquid chromatography to determine respective reaction products quantitatively according to the internal standard method. The results are as follows.

Yield of 2-methyl-4-amino-5-aminomethylpyrimidine: 94.5%
Yield of 2-methyl-4-amino-5-hydroxymethylpyrimidine: 0.3%
Yield of di-(2-methyl-4-amino-5-pyrimidylmethyl)amine: 2.5%

EXAMPLE 9

In a 100 ml autoclave made of stainless steel were introduced 1.37 g (10 mmoles) of 2-methyl-4-amino-5-formylpyrimidine, 24 g of a 20 wt % solution of ammonia in methanol, 0.74 g (5.7 mmoles) of anhydrous nickel chloride and 0.46 g of Stabilized Nickel N103B. After the atmosphere within the system was replaced by nitrogen gas, the temperature of the contents was raised with stirring and maintained at around 90° C. for 30 minutes. Then, hydrogen gas was pressured thereinto at the same temperature so that the pressure might be around 30 Kg/cm$^2$G., and the reaction was carried out at the same temperature followed by quantitative determination of the respective reaction products according to the same procedure as in Example 8. The results are as follows.

Yield of 2-methyl-4-amino-5-aminomethylpyrimidine: 93.8%

Yield of 2-methyl-4-amino-5-hydroxymethylpyrimidine: 0.5%

Yield of di-(2-methyl-4-amino-5-pyrimidylmethyl)amine: 2.5%

EXAMPLE 10

An Experiment was run in the same manner as in Example 9 except that the nickel chloride used in Example 9 was not employed.

Yield of 2-methyl-4-amino-5-aminomethylpyrimidine: 88.3%

Yield of 2-methyl-4-amino-5-hydroxymethylpyrimidine: 4.1%

Yield of di-(2-methyl-4-amino-5-pyrimidylmethyl)amine: 5.8%

EXAMPLE 11

In a 100 ml autoclave made of stainless steel, there were introduced 1.37 g (10 mmoles) of 2-methyl-4-amino-5-formylpyrimidine, 24 g of a 20 wt % solution of ammonia in methanol and 1.34 g (5.4 mmoles) of nickel acetate tetrahydrate. After the atmosphere in the system was replaced by nitrogen gas, the temperature of the contents was raised with stirring and maintained at around 90° C. for one hour. After cooling, the autoclave was opened. Then, a catalyst which had been prepared by developing 2.0 g of a Raney-Nickel (nickel content: around 40 wt %) and washing with water followed by replacement of the water with methanol (methanol: around 6 ml) according to an ordinary method was introduced and the atmosphere in the system was replaced with nitrogen gas. Thereafter, hydrogen gas was pressured thereinto so that the pressure might be around 40 Kg/cm$^2$G. Then, the temperature of the content was raised with stirring and the reaction was carried out with stirring at 90° C. for 2 hours. The results are as follows.

Yield of 2-methyl-4-amino-5-aminomethylpyrimidine: 92.9%

Yield of 2-methyl-4-amino-5-hydroxymethylpyrimidine: 0.6%

Yield of di-(2-methyl-4-amino-5-pyrimidylmethyl)amine: 2.5%

EXAMPLE 12

An experiment was run in the same manner as in Example 8 except that 0.75 g (5.3 mmoles in terms of the total nickel salts) of NiCO$_3$.Ni(OH)$_2$.4H$_2$O was used in place of the nickel chloride in Example 8. The results are as follows.

Yield of 2-methyl-4-amino-5-aminomethylpyrimidine: 93.4%

Yield of 2-methyl-4-amino-5-hydroxymethylpyrimidine: 0.4%

Yield of di-(2-methyl-4-amino-5-pyrimidylmethyl)amine: 2.9%.

EXAMPLE 13

An experiment was run in the same manner as in Example 8 except that 1.51 g (10 mmoles) of 2-ethyl-4-amino-5-formylpyrimidine was used as the starting material in place of the 2-methyl-4-amino-5-formylpyrimidine and 30 g of a 20 wt % solution of ammonia in ethanol was used in place of the 20 wt % solution of ammonia in methanol. The results are as follows.

Yield of 2-ethyl-4-amino-5-aminomethylpyrimidine: 95.1%

Yield of 2-ethyl-4-amino-5-hydroxymethylpyrimidine: 1.5%

Yield of di-(2-ethyl-4-amino-5-pyrimidylmethyl)amine: 2.0%

EXAMPLE 14

In a 100 ml autoclave made of stainless steel, equipped with a high pressure feed pump, there were introduced 11 g of a 20 wt % solution of ammonia in methanol, 0.67 g of Stabilized Nickel (trade name, N103B; manufactured by Nikki Kagaku Co., Ltd.; nickel: around 50 wt %, diatomaceous earth: around 50 wt %) and hydrogen gas so that the pressure might be around 30 Kg/cm$^2$G. The temperature of the mixture was raised with stirring and maintained at 110° C.

In another 100 ml autoclave made of stainless steel, there were introduced 2 g (14.6 mmoles) of 2-methyl-4-amino-5-formylpyrimidine and 24 g of a 20 wt % solution of ammonia in methanol and then the mixture was subjected to reaction with stirring at 90° C. for 2 hours, followed by cooling and opening of the autoclave. The total amount of the thus obtained reaction mixture was pressured over two hours, by using the high pressure feed pump, into the previously prepared mixture which had been maintained at 110° C., and the reaction was continued for 30 minutes at the same temperature.

After completion of the reaction, the autoclave was cooled and the unreacted gases and the like were purged and released from the autoclave. Then, the autoclave was opened and the catalyst therein was collected by filtration. Then, the washing which was obtained by washing the catalyst with methanol was combined with the filtrate and the so combined liquid was concentrated under reduced pressure to remove the ammonia. The pH value of the resultant residue was adjusted at around 3 with a 1N-HCl and the respective reaction products were determined quantitatively by liquid chromatography according to the internal standard method. The results are as follows.

Yield of 2-methyl-4-amino-5-aminomethylpyrimidine: 94.8%

Yield of 2-methyl-4-amino-5-hydroxymethylpyrimidine: 0.6%

Yield of di-(2-methyl-4-amino-5-pyrimidylmethyl)amine: 0.9%

EXAMPLE 15

An experiment was carried out in the same manner as in Example 14 except that the used amount of Stabilized Nickel N103B was changed to be 1.33 g; the used amount of 2-methyl-4-amino-5-formylpyrimidine was changed to be 4 g (29.2 mmoles); and the period of time for continuous feeding under pressure by the use of the high pressure feed pump was changed to be 4 hours. The results are as follows.

Yield of 2-methyl-4-amino-5-aminomethylpyrimidine: 92.9%

Yield of 2-methyl-4-amino-5-hydroxymethylpyrimidine: 0.8%

Yield of di-(2-methyl-4-amino-5-pyrimidylmethyl)amine: 1.5%

EXAMPLE 16

In a 100 ml autoclave made of stainless steel, equipped with a high pressure feed pump, there were introduced 10 g of a mixed solvent of methanol and dioxane (weight ratio, 6 : 4), 2 g of a liquid ammonia, 1.33 g of Stabilized Nickel N103B and hydrogen gas so that the pressure might be 20 Kg/cm$^2$G. Then, the temperature of the mixture was raised with stirring and maintained at 110° C.

On the other hand, in another 100 ml autoclave made of stainless steel, there were reacted 4 g (29.2 mmoles) of 2-methyl-4-amino-5-formylpyrimidine and 25 g of a liquid ammonia in 18 g of a mixed solvent of methanol and dioxane with stirring at 60° C. for 3 hours. After cooling, the autoclave was opened and the excess amount of ammonia was removed. Then, the total amount of the so obtained reaction mixture was introduced under pressure, by using the high pressure feed pump, into the previously prepared mixture which had been maintained at a temperature of 110° C., over 4 hours, and the reaction was continued at the same temperature for 30 minutes.

After completion of the reaction, treatment was carried out in the same manner as in Example 14. The results are as follows.

Yield of 2-methyl-4-amino-5-aminomethylpyrimidine: 90.4%

Yield of 2-methyl-4-amino-5-hydroxymethylpyrimidine: 1.1%

Yield of di-(2-methyl-4-amino-5-pyrimidylmethyl)amine: 1.8%

EXAMPLE 17

In a 100 ml autoclave made of stainless steel, equipped with a high pressure feed pump, there were introduced 12 g of a 20 wt % solution of ammonia in methanol, 0.67 g of Stabilized Nickel N103B and hydrogen gas so that the pressure might be around 30 Kg/cm$^2$G. Then, the temperature of the mixture was raised and maintained at 100° C. with stirring.

On the other hand, in a 100 ml two-necked flask equipped with a gas-inlet tube having a glass filter and a reflux condenser having a silica-gel tube, there were introduced 4 g (29.2 mmoles) of 2-methyl-4-amino-5-formylpyrimidine and 26 g of a 20 wt % solution of ammonia in methanol. While introducing an NH$_3$ gas at a rate of 100 ml/min with stirring, the reaction was carried out at 40° C. for 10 hours followed by cooling. The total amount of the thus obtained reaction mixture was pressured over 4 hours, by the use of the high pressure feed pump, into the previously prepared mixture which had been maintained at 100° C., and the reaction was continued at the same temperature for 30 minutes.

After completion of the reaction, treatment was carried out in the same manner as in Example 14. The results are as follows.

Yield of 2-methyl-4-amino-5-aminomethylpyrimidine: 90.5%

Yield of 2-methyl-4-amino-5-hydroxymethylpyrimidine: 1.1%

Yield of di-(2-methyl-4-amino-5-pyrimidylmethyl)amine: 1.6%

EXAMPLE 18

In a 100 ml autoclave made of stainless steel, equipped with a high pressure feed pump, there were introduced a catalyst which had been prepared by developing 2 g of a Raney-Nickel (nickel content: around 40 wt %) and washing with water according to an ordinary method followed by replacement of the water with methanol (methanol: around 12 g), 3 g of a liquid ammonia and hydrogen gas so that the pressure might be around 30 Kg/cm$^2$G. Then, the temperature of the mixture was raised with stirring and maintained at 90° C.

On the other hand, in another 100 ml autoclave made of stainless steel, there were introduced 2 g (14.6 mmoles) of 2-methyl-4-amino-5-formylpyrimidine and 28 g of a 20 wt % solution of ammonia in methanol, and the reaction was carried out at 90° C. for 2 hours with stirring. After cooling, the autoclave was opened. Then, the total amount of the thus obtained reaction mixture was pressured over 2 hours, by using the high pressure feed pump, into the previously prepared mixture which had been maintained at 90° C. and the reaction was continued at the same temperature for 30 minutes.

After completion of the reaction, treatment was conducted in the same maner as in Example 14. The results are as follows.

Yield of 2-methyl-4-amino-5-aminomethylpyrimidine: 91.7%

Yield of 2-methyl-4-amino-5-hydroxymethylpyrimidine: 1.8%

Yield of di-(2-methyl-4-amino-5-pyrimidylmethyl)amine: 1.2%

We claim:

1. A process for the preparation of a 2-alkyl-4-amino-5-aminomethylpyrimidine which comprises reacting a 2-alkyl-4-amino-5-formylpyrimidine or a salt of a mineral acid thereof with hydrogen and ammonia in an amount of at least 4 moles of ammonia per one mole of the 2-alkyl-4-amino-5-formylpyrimidine or salts thereof (a) in the presence of a reduction catalyst selected from the group consisting of palladium supported on activated carbon, nickel-diatomaceous earth, platinum supported on alumina, copperchromium powder and Raney nickel and (b) in the presence of at least one salt of divalent nickel or hydrate thereof.

2. The process as claimed in claim 1, wherein the hydrogen is used in an amount of 5 to 400 moles per one mole of the 2-alkyl-4-amino-5-formylpyrimidine.

3. The process as claimed in claim 1, wherein the reduction catalyst is used in an amount of 0.001 to 3 gram atoms in terms of the metal, per one mole of the 2-alkyl-4-amino-5-formylpyrimidine.

4. The process as claimed in claim 1, wherein the reaction is carried out at a temperature of 0 to 200° C.

5. The process as claimed in claim 1, wherein the ammonia is used in the form of a liquid ammonia, an ammonia gas or an aqueous ammonia.

6. The process as claimed in claim 1, wherein the salt of divalent nickel or hydrate thereof is used in an amount of 0.1 to 5 moles per one mole of the 2-alkyl-4-amino-5-formylpyrimidine or salt thereof.

7. The process as claimed in claim 1, wherein the hydrogen is used in an amount of 5 to 400 moles per one mole of the 2-alkyl-4-amino-5-formylpyrimidine or salt thereof.

8. The process as claimed in claim 1, wherein the reduction catalyst is used in an amount of 0.001 to 3 gram atoms in terms of the metal, per one mole of the 2-alkyl-4-amino-5-formylpyrimidine or salt thereof.

9. The process as claimed in claim 1, wherein the reaction is carried out at a temperature of 0° to 200° C.

10. The process as claimed in claim 1, wherein the ammonia is used in the form of a liquid ammonia, an ammonia gas or an aqueous ammonia.

11. The process as claimed in claim 1, which comprises reacting the 2-alkyl-4-amino-5-formylpyrimidine or salt thereof with ammonia in a first inert solvent to form a reaction product; reacting said reaction product, without isolating the same from the reaction mixture, with a second inert solvent containing ammonia, hydrogen and the reduction catalyst to reduce said reaction product and thereby obtain 2-alkyl-4-amino-5-aminomethylpyrimidine.

12. The process as claimed in claim 11, wherein the ammonia used for the reaction with the 2-alkyl-4-amino-5-formylpyrimidine is in the form of a liquid ammonia, an ammonia gas or an aqueous ammonia.

13. The process as claimed in claim 11, wherein the first solvent is used in an amount of 3 to 30 parts by weight per one part by weight of the 2-alkyl-4-amino-5-formylpyrimidine or salt thereof.

14. The process as claimed in claim 11, wherein the reaction of the 2-alkyl-4-amino-5-formylpyrimidine with ammonia is carried out at a temperature of 0 to 130° C. under a partial pressure of ammonia of 1 to 100 Kg/cm$^2$G.

15. The process as claimed in claim 11, wherein the reduction catalyst is used in an amount of 0.001 to 3 gram atoms in terms of the metal, per one mole of the 2-alkyl-4-amino-5-formylpyrimidine or salt thereof.

16. The process as claimed in claim 11, wherein the reaction is carried out at a temperature of 0 to 200° C.

17. The process as claimed in claim 11, wherein the ammonia contained in the second inert solvent is used in the form of a liquid ammonia, an ammonia gas or an aqueous ammonia in an amount of 4 to 300 moles per one mole of the 2-alkyl-4-amino-5-formylpyrimidine or salt thereof.

18. The process as claimed in claim 11, wherein the hydrogen is used in an amount of 5 to 400 moles per one mole of the 2-alkyl-4-amino-5-formylpyrimidine or salt thereof.

19. The process as claimed in claim 11, wherein the second solvent is used in an amount of 2 to 20 parts by weight per one part by weight of the 2-alkyl-4-amino-5-formylpyrimidine or salt thereof.

20. The process of claim 15, wherein said reduction catalyst is used in an amount of from 0.002 to 2 gram atoms in terms of metal, per one mole of the 2-alkyl-4-amino-5-formylpyrimidine or salt thereof.

21. The process of claim 1, wherein the salt of divalent nickel or hydrate thereof is selected from the group consisting of nickel chloride, nickel bromide, nickel sulfate, nickel nitrate, nickel phosphate, nickel carbonate, nickel hydroxide, nickel acetate, nickel oxalate, nickel benzoate, nickel ammonium chloride, nickel ammonium sulfate, and nickel potassium sulfate.

22. The process of claim 1, wherein the amount of said salt is from 0.1 to 5 moles per one mole of 2-alkyl-4-amino-5-formylpyrimidine or salt thereof.

23. The process of claim 11, wherein said first and second inert solvent are individually selected from the group consisting of methanol, ethanol, propanol, butanol, dioxane, tetrahydrofuran, diethylether, benzene, toluene, xylene, hexane, cyclohexane and water.

24. The process of claim 1 wherein the amount of ammonia is from 4 to 500 moles per mole of the 2-alkyl-4-amino-5-formylpyrimidine.

25. A process for the preparation of a 2-alkyl-4-amino-5-aminomethylpyrimidine which comprises reacting a 2-alkyl-4-amino-5-formylpyrimidine or salt thereof with ammonia in a first inert solvent to form a reaction product; reacting said reaction product, without isolating the same from the reaction mixture, with a second inert solvent containing ammonia, hydrogen and the reduction catalyst to reduce said reaction product and thereby obtain 2-alkyl-4-amino-5-aminomethylpyrimidine, said ammonia being in an amount of at least 4 moles of ammonia per one mole of the 2 alkyl-4-amino-5-formylpyrimidine or salts thereof, and said reduction catalyst being selected from the group consisting of palladium supported on activated carbon, nickel-diatomaceous earth, platinum supported on alumina, copper-chromium powder and Raney nickel.

26. A process for the preparation of a 2-alkyl-4-amino-5-aminomethylpyrimidine which comprises simultaneously reacting (i) a 2-alkyl-4-amino-5-formylpyrimidine or a salt of a mineral acid thereof with (ii) hydrogen and (iii) ammonia in an amount of at least 4 moles of ammonia per one mole of the 2-alkyl-4-amino-5-formylpyrimidine or salts thereof in the presence of a reduction catalyst selected from the group consisting of palladium supported on alumina, copper-chromium powder and Raney nickel.

* * * * *